United States Patent
Sohn et al.

(10) Patent No.: US 7,632,473 B2
(45) Date of Patent: Dec. 15, 2009

(54) PROCESS AND APPARATUS FOR ALKYLATION OF AROMATIC WITH OLEFIN USING IMPURE AROMATIC RECYCLE

(75) Inventors: Stephen W. Sohn, Des Plaines, IL (US); Michael R. Smith, Des Plaines, IL (US); Lance A. Baird, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/021,324

(22) Filed: Jan. 29, 2008

(65) Prior Publication Data

US 2008/0118415 A1 May 22, 2008

Related U.S. Application Data

(62) Division of application No. 11/042,587, filed on Jan. 25, 2005, now Pat. No. 7,396,968.

(51) Int. Cl.
*B01J 8/00* (2006.01)
*B01J 7/02* (2006.01)
*C07C 15/067* (2006.01)

(52) U.S. Cl. .................. 422/234; 422/236; 585/450

(58) Field of Classification Search ............ 585/450; 422/234, 236
See application file for complete search history.

(56) References Cited

U.S. PATENT DOCUMENTS

| | | | | |
|---|---|---|---|---|
| 3,381,049 A | * | 4/1968 | Alexander et al. | 585/448 |
| 4,051,191 A | | 9/1977 | Ward | 260/671 R |
| 4,108,914 A | | 8/1978 | Gewartowski | 260/671 R |
| 4,463,205 A | | 7/1984 | Spinner | 585/455 |
| 5,073,653 A | * | 12/1991 | Butler | 585/449 |
| 5,777,187 A | | 7/1998 | Knifton et al. | 585/449 |
| 6,069,285 A | | 5/2000 | Fritsch et al. | 585/449 |
| 6,835,862 B1 | | 12/2004 | Gajda et al. | 585/467 |

* cited by examiner

*Primary Examiner*—Thuan Dinh Dang
(74) *Attorney, Agent, or Firm*—Arthur E Gooding (57) ABSTRACT

Processes and apparatus for the alkylation of aromatic compound with mono-olefin aliphatic compound in the presence of solid alkylation catalyst use a lights distillation for obtaining desired selectivities to arylalkane in a energy efficient manner. The processes and apparatus offer the potential for debottlenecking existing arylalkane production facilities and reducing the size and energy requirements for a new arylalkane production facility.

5 Claims, 4 Drawing Sheets

PROCESS AND APPARATUS FOR ALKYLATION OF AROMATIC WITH OLEFIN USING IMPURE AROMATIC RECYCLE

CROSS REFERENCE TO RELATED APPLICATION

This application is a Division of prior copending application Ser. No. 11/042,587, filed Jan. 25, 2005, which is incorporated herein by reference in its entirety.

FIELD OF THE INVENTION

This invention relates to processes and apparatus for the alkylation of aromatic compound with aliphatic mono-olefin compound in which the aromatic compound is provided in a stoichiometric excess and unreacted aromatic compound is recycled.

BACKGROUND TO THE INVENTION

Alkylation of aromatic compounds produces arylalkanes that may find various commercial uses, e.g., alkylbenzenes that can be sulfonated to produce detergents. In the alkylation process, aromatic compound is reacted with olefin of the desired molecular weight to produce the sought arylalkane. The alkylation conditions comprise a catalyst such as aluminum chloride, hydrogen fluoride, or zeolitic catalysts and elevated temperature.

The alkylation, however, is not selective and can produce dimers, dialkylaryl compounds and diaryl compounds ("heavies") and can affect skeletal isomerization of the olefin, resulting in a loss of selectivity to the sought arylalkane structure. The formation of dialkylaryl compounds is particularly problematic as the reaction approaches complete conversion of the olefin and the greater concentration of the arylalkane since the likelihood has increased that an olefin molecule will react with an arylalkane molecule rather than a molecule of the aromatic compound in the feed. Accordingly, typical processes use a large excess of aromatic compound to enhance selectivity to arylalkane over dialkylaryl compound. In many instances, the mole ratio of aromatic compound to olefin is greater than 15:1.

In order to provide an economically viable process, the unreacted aromatic compound must be recovered from the alkylation product and recycled. Typical commercial processes recover the aromatic compound during refining the alkylation product through the use of several distillation steps. For instance, see Pujado, Linear Alkylbenzene (LAB) Manufacture, Handbook of Petroleum Refining Processes, Second Edition, pp 1.53 to 1.66 (1996), especially pages 1.56 to 1.60, who discloses refining processes for linear alkylbenzenes. In general, benzene and an olefin-containing feedstock derived from a paraffin dehydrogenation are reacted to produce an alkylation reaction product. The reaction product is refined. A first distillation in a benzene column separates a benzene stream as an overhead stream for recycling to the alkylation reactor. The bottoms stream from the benzene column is virtually free of benzene and is then subjected to a distillation to separate paraffins and unreacted olefin in a paraffins column. The paraffins-containing overhead is capable of being recycled to the paraffin dehydrogenation unit while the bottoms stream is passed to a heavy alkylate distillation column. In the heavy alkylate distillation column, heavies are separated from the lighter alkylbenzene, and a heavies-containing stream is withdrawn as a bottoms stream.

If desired, the bottoms stream can be subjected to a further distillation to recover additional alkylbenzene.

An important consideration for commercial-scale facilities for production of arylalkanes, especially alkylbenzene, is energy and equipment integration. For example, reboilers for distillation columns are conventionally heated with a thermal stream, e.g., hot oil or other thermally-stable liquid, derived from a central heater. The capacity of a distillation column, at a given degree of separation, can thus be limited by the availability of thermal fluid. For an alkylbenzene process having a refining system comprising a benzene column, paraffins column and heavy alkylate column, the benzene column consumes the greatest portion of the reboiler heat. Thus the heat demand or reboiler size for the benzene distillation can provide a bottleneck to increased capacity at a given benzene to olefin feed ratio to the alkylation reactor. Similarly, the size of the benzene column itself can pose a bottleneck.

Significant economic benefits can be achieved through even slight improvements in efficiency or reductions in energy consumption or increases in production capacity in a given existing plant, e.g., through debottlenecking, provided that no undue increase in the production of heavies occurs and the arylalkyl meets specifications after refining.

Fritsch, et al., in U.S. Pat. No. 6,069,285 disclose the use of a benzene rectifier and a benzene fractionation column to treat effluent from an aromatic alkylation process using solid alkylation catalyst. The rectifier provides an overhead containing feed aromatics and a rectifier bottom stream comprising feed aromatics and enriched in alkylaromatics. The overhead stream from the rectifier is recycled to an on-stream alkylation reactor. The benzene column produces higher purity benzene-containing overhead stream that can be used to regenerate a sorption bed to treat the olefin-containing feed prior to being passed to the alkylation reactor and can be used to regenerate solid alkylation catalyst in an off-stream alkylation reactor.

Processes and apparatus are sought to effect alkylation that reduce the size and heat demand of the distillation system to remove aromatics from the alkylation reaction product at a given production rate. The processes and apparatus would thus allow the debottlenecking of existing facilities and the design of new facilities with a smaller aromatics removal column.

SUMMARY OF THE INVENTION

In accordance with this invention, it has been found that viable aromatic alkylation processes can be provided wherein a portion of the aromatic compound recycled is impure. In the processes and apparatus of this invention, a lights distillation is used to recover a portion of the unreacted aromatic compound contained in the effluent from an alkylation reaction zone. The aromatic compound recovered by the lights distillation is recycled to the alkylation reaction zone, and the remaining portion of the unreacted aromatic compound is recovered in a subsequent distillation. The column size and energy requirements for the subsequent distillation are thus reduced. Because the lights distillation need not provide a relatively pure aromatic stream, the energy requirements and size of the lights distillation can be commercially viable. Often, the lights distillation is effected using less than 5 theoretical distillation trays, especially a flash distillation. Thus, the overhead can contain appreciable amounts of arylalkane product as well as paraffins, if paraffins are present in the alkylation reactor effluent. Although arylalkane can be reacted to produce heavies under alkylation conditions, the processes of this invention can still provide an alkylation reaction effluent without an undue amount of heavies.

In one broad aspect of the processes of this invention, the process for the alkylation of aromatic compound of 6 to 8 carbon atoms with an aliphatic mono-olefin of 8 to 18 carbon atoms comprises:
 a. co-currently passing said aromatic compound, said aliphatic compound and paraffin of between 8 and 18 carbon atoms to an alkylation zone comprising solid alkylation catalyst under liquid phase alkylation conditions to produce an effluent comprising arylalkane, aromatic compound and paraffin, the mole ratio of said aromatic compound to said aliphatic compound passed to the alkylation zone being at least about 6:1, preferably at least about 10:1 or 15:1 and said paraffin passed to said alkylation zone being in a mole ratio to said aliphatic compound of between about 1:1 to 20:1, preferably 8:1 to 15:1;
 b. distilling a distillation feed comprising at least a portion of the effluent of step a, said distillation being conducted with less than about 5, preferably less than 2, theoretical distillation trays, and most preferably flash distillation, at a pressure of less than about 500 kPa absolute with less than about 40 kcal, preferably less than about 30 kcal, of heat being externally supplied per kilogram of distillation feed so as to provide an overhead comprising between about 20 and 98, frequently between about 50 and 95, weight percent of the aromatic compound contained in said at least a portion of the effluent and arylalkane, and a bottoms stream comprising aromatic compound and at least about 80, preferably at least about 90, weight percent of the arylalkane contained in said at least a portion of the effluent,
 c. recycling the overhead from step b to the alkylation zone of step a, and
 d. distilling a second distillation feed comprising bottoms stream from step b under distillation conditions sufficient to provide an overhead comprising aromatic compound and a bottoms stream comprising arylalkane having an essential absence of aromatic compound. Often the overhead from step b contains at least about 0.1 weight percent arylalkane, e.g., up to about 5 weight percent arylalkane, for instance, 0.2 to 2, weight percent arylalkane, based on the weight of the overhead. In a preferred mode, at least a portion of the overhead from step d is recycled to step a. Preferably the bottoms stream of step d contains less than 50 parts per million by weight aromatic compound.

In more preferred aspects of the processes of this invention, the distillation of step b is conducted at a lower pressure than the alkylation zone, and is often at between about 80 and 250 kPa absolute. Advantageously the pressure of the distillation of step b is sufficiently lower than that of the effluent from the alkylation zone that a significant portion of the aromatic compound in the at least a portion of the effluent fed to the first distillation zone, is vaporized.

In another broad aspect of the processes of this invention, the processes for the alkylation of aromatic compound of 6 to 8 carbon atoms with an olefin-containing aliphatic compound of 8 to 18 carbon atoms comprise:
 a. co-currently passing said aromatic compound and said aliphatic compound to an alkylation zone comprising solid alkylation catalyst under liquid phase alkylation conditions to produce an effluent comprising arylalkane and aromatic compound, the mole ratio of said aromatic compound passed to the alkylation zone to said aliphatic compound passed to the alkylation zone being at least about 6:1, preferably at least about 10:1 or 15:1;
 b. distilling at least a portion of the effluent of step a under flash distillation conditions including a lower pressure than that of the alkylation zone to provide at least an overhead and a bottoms stream, said overhead comprising about 20 to 98 weight percent of the aromatic compound in said at least a portion of the effluent and arylalkane, and said bottoms stream comprising at least about 80 weight percent of the arylalkane contained in the at least a portion of the effluent, and
 c. recycling the overhead of step b to the alkylation zone of step a.

In yet another broad aspect of the processes of this invention, the processes for the alkylation of aromatic compound of 6 to 8 carbon atoms with an olefin-containing aliphatic compound of 8 to 18 carbon atoms comprise:
 a. co-currently passing said aromatic compound, said aliphatic compound and paraffin of between 8 and 18 carbon atoms to an alkylation zone comprising solid alkylation catalyst under liquid phase alkylation conditions to produce an effluent comprising arylalkane, aromatic compound and paraffin, the mole ratio of said aromatic compound to said aliphatic compound passed to the alkylation zone being at least about 6:1 and preferably at least about 10:1 and said paraffin passed to said alkylation zone being in a mole ratio to said aliphatic compound of between about 1:1 to 20:1;
 b. distilling a distillation feed comprising at least a portion of the effluent of step a, said distillation being conducted with less than about 5 theoretical distillation trays to provide an overhead comprising between about 20 and 98 weight percent of the aromatic compound contained in said at least a portion of the effluent and arylalkane, and a bottoms stream comprising aromatic compound and at least about 80 weight percent of the arylalkane contained in said at least a portion of the effluent,
 c. recycling the overhead from step b to the alkylation zone of step a,
 d. distilling a second distillation feed comprising bottoms stream from step b under distillation conditions sufficient to provide an overhead comprising aromatic compound and a bottoms stream comprising arylalkane having an essential absence of aromatic compound, and
 e. withdrawing from at least one of steps a, b and c, sufficient fluid to maintain the concentration of paraffin in the effluent from the alkylation zone at less than about 50 weight percent and passing said fluid to the distilling of step d.

Thus, the processes of this invention can reduce the amount of aromatic compound passing to a refining system for the arylalkane. Therefore, for instance, the size of the aromatic compound distillation for an existing facility can readily be debottlenecked, and for a grass roots facility, the aromatic compound distillation can be designed to be smaller and require less reboiler demand. Advantageously the distillation of step b does not need to achieve a high degree of separation of the aromatic compound from the arylalkane to achieve these advantages or to achieve desirable arylalkane product quality.

In the broad aspects of the apparatus of this invention for alkylation of aromatic compound with olefin-containing aliphatic compound, the apparatus comprises:
 a. an alkylation reactor having an inlet portion in fluid communication with a supply of olefin-containing aliphatic compound and an outlet portion, said reactor having a chamber containing solid alkylation catalyst such that fluid passing between the inlet portion and the outlet portion contacts the catalyst;

b. a first distillation column having an inlet in fluid communication with the outlet of the reactor, an overhead outlet in fluid communication with the inlet portion of the reactor, and a bottoms stream outlet, said first distillation column having less than 5 theoretical distillation plates; and c. a second distillation column having an inlet in fluid communication with the bottoms stream outlet of the first distillation column, an overhead outlet in fluid communication with the inlet portion of the reactor, and a bottoms stream outlet, in which the second distillation column has greater than 5 theoretical distillation plates.

DETAILED DISCUSSION

The Feed and Products:

Aliphatic mono-olefins and aromatic compounds are used for the alkylation process. The selection of the olefin and aromatic compounds is dependent upon the sought alkylation product.

The olefin-containing aliphatic compound is preferably of about 8 to 18, often for detergent applications, 9 to 16, carbon atoms. The positioning of the olefinic bond in the molecule is not critical as most alkylation catalysts have been found to promote migration of the olefinic bond. However, the branching of the hydrocarbon backbone is often more of a concern as the structural configuration of the alkyl group on the arylalkane product can affect performance. For instance, where alkylbenzenes are sulfonated to produce surfactants, undue branching can adversely affect the biodegradability of the surfactant. On the other hand, some branching may be desired such as the lightly branched modified alkylbenzenes such as described in U.S. Pat. No. 6,187,981. The olefin may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms.

The olefin-containing aliphatic compound is usually a mixture of two or more olefins. For commercial processes, other components may be present with the olefin-containing aliphatic compound. For instance, the olefin may be obtained by the dehydrogenation of a paraffinic feedstock and unreacted paraffin, which is difficult to separate from the olefin, is passed to the alkylation reactor. See, for instance, U.S. Pat. No. 6,670,516, herein incorporated by reference. Generally, where olefin is obtained by the dehydrogenation of a paraffinic feedstock, the molar ratio of olefin to paraffin is between about 1:12 to 1:8; however, such amounts of paraffin are not critical to the processes of this invention. Indeed, olefin-containing feedstocks having an essential absence of paraffins are suitable. However, the processes of this invention are particularly useful where paraffin is present as a significant portion of the energy and size of the distillation of step d is devoted to separating aromatic compound from paraffin. The processes of this invention thus have a beneficial effect in reducing the energy consumption and size of that distillation.

The source of the paraffinic feedstock for dehydrogenation is not critical although certain sources of paraffinic feedstocks will likely result in the impurities being present. Conventionally, kerosene fractions produced in petroleum refineries either by crude oil fractionation or by conversion processes therefore form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds.

The paraffinic feedstock may alternatively be at least in part derived from oligomerization or alkylation reactions. Such feed mixture preparation methods are inherently imprecise and produce a mixture of compounds. The feed mixtures to the process may contain quantities of paraffins having multiple branches and paraffins having multiple carbon atoms in the branches, cycloparaffins, branched cycloparaffins, or other compounds having boiling points relatively close to the desired compound isomer. Thus, the feed mixtures to the process of this invention can also contain sizable quantities of aromatic hydrocarbons.

Another source of paraffins is in condensate from gas wells. Usually insufficient quantities of such condensate are available to be the exclusive source of paraffinic feedstock. However, its use to supplement other paraffinic feedstocks can be desirable. Typically these condensates contain sulfur compounds, which have restricted their use in the past. As this invention enables the use of sulfur-containing feeds, these condensates can be used to supply paraffins for alkylation.

Paraffins may also be produced from synthesis gas (Syngas), hydrogen and carbon monoxide. This process is generally referred to as the Fischer-Tropsch process. Syngas may be made from various raw materials including natural gas and coal, thus making it an attractive source of paraffinic feedstock where petroleum distillates are not available.

The olefin-containing feed to the alkylation reactor should be sufficiently free of impurities, such as water, nitrogen compounds and sulfur compounds, that can unduly adversely affect the life of the alkylation catalyst.

The aromatic-containing feedstock to the subject process comprises a phenyl compound, which is benzene when the process is detergent alkylation. In a more general case, the phenyl compound of the aromatic feedstock may be alkylated or otherwise substituted derivatives or of a higher molecular weight than benzene, including toluene, ethylbenzene, xylene, etc., but the product of such an alkylation may not be as suitable a detergent precursor as alkylated benzenes.

Alkylation:

The olefin is reacted with aromatic compound to produce arylalkane. Usually the aromatic compound is present in a significant stoichiometric excess to the olefin, e.g., from about 6:1 or from about 10:1 or 15:1 up to about 50:1 and normally from about 15:1 to about 30:1, on a molar basis.

The aromatic compound and the olefin are reacted under alkylation conditions in the presence of a solid alkylation catalyst. These alkylation conditions generally include a temperature in the range between about 80° C. and about 200° C., most usually at a temperature not exceeding about 175° C., say, about 125° C. to 160° C. Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin, the aryl compound, and temperature, but normally is in the range of about 1300 to 7000 kPa(g), and most usually between about 2000 and 3500 kPa(g). Preferably the alkylation conditions do not substantially result in skeletal isomerization of the olefin. For instance, less than 15 mole percent, and preferably less than 10 mole percent, of the olefin, the aliphatic alkyl chain, and any reaction intermediate undergoes skeletal isomerization.

Alkylation of the aromatic compound by the olefins is conducted in a continuous manner using one bed or two or more catalyst beds in flow series. For purposes herein, a catalyst bed is termed a reactor whether in the same or a separate vessel from another bed. Each reactor has an inlet portion and an outlet portion. The reactants may be in admixture prior to entering the inlet portion of the reactor, or they may be individually introduced and mixed in the reactor.

The catalyst may be used as a packed bed or a fluidized bed. The feed to the reaction zone may be passed either upflow or downflow, or even horizontally as in a radial bed reactor; however, the flows of the aromatic compound and olefin-containing aliphatic compound are co-current. In one desirable variant, olefin-containing feedstock may be fed into several discrete points within the reaction zone, and at each zone the aromatic compound to olefin molar ratio may be greater than 50:1. The total feed mixture, that is, aromatic compound plus olefin, is often passed through the packed bed at a liquid hourly space velocity (LHSV) between about 0.3 and about 6 or 10 hr-1 depending upon, e.g., alkylation temperature and the activity of the catalyst. Lower values of LHSV within this range are preferred. It is usually desired that sufficient residence time in the reaction zone be used such that at least about 98, and often at least about 99.5, mole percent of the olefin is reacted.

Any suitable alkylation catalyst may be used in the present invention, provided that the requirements for conversion, selectivity, and activity are met. Preferred alkylation catalysts comprise zeolites having a zeolite structure type selected from the group consisting of BEA, MOR, MTW, and NES. Such zeolites include mordenite, ZSM4, ZSM-12, ZSM-20, offretite, gmelinite, beta, NU-87, and gottardite. Clay or amorphous catalysts including silica-alumina and fluorided silica-alumina may also find utility. Further discussion of alkylation catalysts can be found in U.S. Pat. Nos. 5,196,574; 6,315,964 and 6,617,481.

The Lights Distillation Recycle:

In accordance with this invention at least a portion of an alkylation reactor effluent is subjected to a lights distillation to recover as overhead a fraction of the unreacted aromatic compound. The recovered aromatic compound is recycled to the alkylation reactor. Thus, the use of the lights distillation reduces the amount of aromatic compound in the reaction product passed to the refining system including a distillation assembly for removing aromatic compound from the arylalkane.

In the processes of the invention, one or more alkylation reactor beds may be used with the lights distillation overhead being recycled to the inlet portion of the reactor from which the effluent is obtained for the light distillation or of an upstream alkylation reactor. The amount of the effluent directed to the light distillation may be as little as 20 weight percent of the total effluent or may comprise the entire effluent stream. Where it is desired to debottleneck an existing manufacturing plant, even directing a small amount of the effluent to the light distillation can be beneficial. Often at least about 50, and sometimes at least about 80, weight percent of the effluent is subjected to the light distillation.

In any event, sufficient reaction product must be removed from the alkylation reaction zone and the lights distillation loop to prevent an undue build-up of paraffin or other inerts in the loop. Typically the concentration of paraffin in the alkylation zone or the alkylation zone effluent is less than about 50 weight percent, and preferably less than about 40, e.g., less than about 35, weight percent. If more than one reactor is used, most preferably it is the effluent from the first reactor that is subjected to the lights distillation with the overhead from the lights distillation being recycled to the inlet portion of that reactor.

Only a portion of the aromatic compound contained in the distillation feed to the lights distillation zone is intended to be recovered in the overhead of the lights distillation. The amount of the aromatic compound recovered in the overhead is often between about 20 and 98, say, 60 or 75 to 98, weight percent of that in the distillation feed. The overhead may also contain arylalkane, unreacted olefin, aromatic by-products and paraffins, especially where the olefin is supplied in combination with paraffins.

The recycling of paraffins, can lead to a higher concentration of the paraffins in the alkylation reactor at steady state conditions than in the olefin-containing feed to the alkylation reactor which needs to be taken in account in reactor sizing. Normally where paraffins are present, less than about 60, preferably less than about 40, and often between about 5 and 30, weight percent of the paraffins in the distillation feed is contained in the overhead. Generally less than about 60, often between about 5 and 30, weight percent of the unreacted olefin-containing compound fed to the lights distillation will be in the overhead.

Advantageously, the distillation equipment need not be extensive to effect such recovery, e.g., the distillation may be accomplished with less than about 5 theoretical distillation plates. Moreover, the lights distillation is preferably conducted without significant reboiler heat, and indeed, in some instances, the sought recovery of aromatic compound may be accomplished by a flash distillation due to a pressure drop of the effluent from alkylation reaction conditions without the need for a heat source. The feed to the lights distillation may be at any convenient temperature. For instance, it may be at or close to the temperature of the effluent from the alkylation reaction zone, or it may be heated or cooled by indirect heat exchange. Generally the temperature of the distillation feed is below about 300° C., say 100° to 275° C. Where heat is externally supplied to the lights distillation, e.g., to provide for internal reflux in a fractionation column, it preferably is less than about 40, more preferably less than about 30, kilocalories (kcal) per kilogram of the feed to the lights distillation. As used herein, externally supplied heat is heat supplied to the lights distillation, excluding heat supplied with the lights distillation feed.

The bottoms temperature of the lights distillation zone is usually in the range of about 80° C. to 150° C., preferably between about 90° C. and 140° C., and the pressure in the lights distillation zone is typically between about 70 and 300, preferably between about 90 and 250, say, 100 and 200, kPa absolute. Where a reflux is used, the rate of external reflux (distillation feed to reflux, F/R) is preferably between about 0.1:1 to 5:1, more preferably between about 0.4:1 and 0.8:1, kilogram per kilogram of effluent fed to the lights distillation zone.

The lights distillation may be effected in an open vessel for a flash distillation or may contain suitable trays or packing for a fractionation. A flash distillation may contain a demister to prevent liquid carryover in the overhead. Heat to the lights distillation zone may be provided by indirect heat exchange at the bottom of the zone, or by withdrawing, heating and recycling to the base of the column a portion of the liquid contained at the bottom of the lights distillation zone. Alternatively or additionally, the distillation feed may be heated, but preferably not to a temperature that may cause undue reaction or degradation of the arylalkane, e.g., below about 300° C.

The composition of the overhead from the lights distillation is primarily dependent upon the composition of the distillation feed, the temperature and pressure for the lights distillation, the reflux ratio and the practical distillation plates contained in the lights distillation zone. The practical distillation plates are determined from the actual performance of the distillation column.

The overhead form the lights distillation may be cooled to cause condensation and then the liquid pumped to the inlet portion of the designated alkylation reactor. If desired, a portion of the condensed liquid may be used as reflux for the lights distillation.

The lights distillation will provide at least a bottoms stream containing arylalkane. When the lights distillation is other than a flash distillation, one or more midcuts can also be taken. If no midcuts are taken, the composition of the bottoms stream will simply be the balance of the feed to the lights distillation column. If one or more midcuts are taken, the composition of the bottoms stream would differ. Usually the bottoms stream will contain at least about 80, and often at least about 90 or even 95 or more, weight percent of the arylalkane in the effluent fed to the lights distillation column. The bottoms stream will also contain aromatic compound, e.g., at least about 0.5, say, 1 to 80, weight percent of the aromatic compound in the distillation feed. Where no midcut is taken and paraffin is present, the bottoms stream will contain paraffin, usually in an amount of at least 40, say 45 to 95, weight percent of the paraffin contained in the distillation feed.

The processes of this invention provide not only for energy efficient recycling of large amounts of aromatic compound to the alkylation reactor to provide for desired selectivities to the sought arylalkane product and for debottlenecking of existing arylalkane production facilities, but also they enable flexibility in the manner in which the arylalkane is purified. See, for instance, the discussion of FIG. 4 below.

In common commercial configurations, the alkylation reactor effluent would be passed to a distillation assembly that separates as a relatively pure stream the aromatic compound contained in the effluent. The bottoms stream from this distillation assembly would then be passed to a distillation assembly to separate as the overhead, paraffins and unreacted olefins, and the bottoms from this second distillation assembly would be fed to a heavies distillation assembly where the arylalkane product is contained in the overhead. If desired, a finishing column may be used to further purify the arylalkane, especially after a clay treatment to remove color formers. In this type of distillation train, the bottoms stream of the lights distillation is normally fed to the distillation assembly for separating the aromatic compound.

For purposes of illustration only, the following disclosure references the production of alkylbenzene. In an alkylbenzene refining system, the benzene distillation is generally conducted with a bottoms temperature of less than about 300° C., preferably less than about 275° C., usually between about 230° and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column in the benzene distillation assembly may contain any convenient packing or distillation trays, but most often trays such as sieve and bubble trays, are used. Often the assembly provides at least about 5, say 6 to 70, and preferably 20 to 50, theoretical distillation plates. The reflux ratio (herein defined as the distillate to reflux weight ratio) is often in the range of about 2:1 to 1:10, preferably about 1.5:1 to 1:5. The bottoms stream from the benzene distillation generally contains less than about 1000 ppmw, preferably less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., preferably less than about 275° C., usually between about 250° C. and 275° C., and at a pressure at which overhead is provided of between about 5 and 110, preferably between about 10 and 50, kPa absolute. The column may contain any convenient packing or distillation trays, but most often sieve trays are used. Often the paraffins distillation assembly provides at least about 5, say 7 to 20, theoretical distillation plates. The reflux ratio is often in the range of about 3:1 to 1:10, preferably about 1:1 to 1:3. The bottoms stream from the paraffins distillation generally contains less than about 5000, preferably less than about 500, parts by million by weight (ppmw) paraffins and preferably less than about 10, often less than about 1, ppmw benzene. The paraffins distillation may occur in a single column or two or more distinct columns may be used.

The heavy alkylate distillation is generally conducted with a bottoms temperature of less than about 300° C., preferably less than about 275° C., usually between about 250° C. and 275° C., and at a pressure of between about 0.5 and 30, preferably between about 1 and 5, kPa absolute. The column may contain any convenient packing or distillation trays, but most often structured packing is used. Often the heavy alkylate distillation assembly provides at least about 5, say 10 to 30, and preferably 10 to 20, theoretical distillation plates. The reflux ratio is often in the range of about 2:1 to 1:5, preferably about 0.2:1 to 1:1. The overhead from the heavy alkylate distillation generally contains less than about 1000, preferably less than about 100 ppmw, and sometimes less than about 50 ppmw, total heavies.

The refining system may contain additional distillation zones, e.g., to recover additional arylalkane from heavies.

The invention will be further illustrated by reference to the drawings, which are riot in limitation of the scope of the invention. The drawings will be discussed in terms of the production of alkylbenzene from benzene and an olefin-containing feed which is a dehydrogenated paraffin feedstock for the sake of ease of reference; however, the broad aspects of the invention are not limited to such feedstocks.

Figure 1:
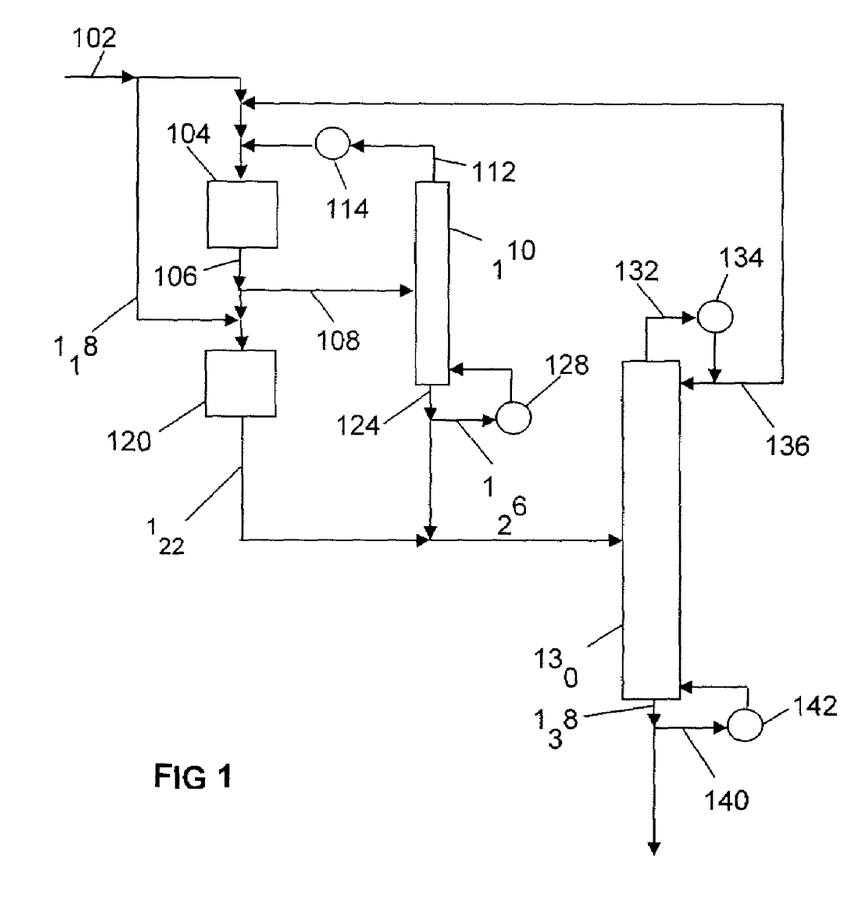
FIG. 1 is a schematic representation of an apparatus adapted to practice a process in accordance with this invention in which two alkylation reactors are provided and the feed for the lights distillation is obtained from the effluent from the first reactor.

With reference to FIG. 1, an olefin-containing feedstock is supplied via line 102 to a first alkylation reactor 104. Effluent from alkylation reactor 104 passes via line 106 to a second alkylation reactor 120. Under normal operation, at least about 90 percent by weight of the olefin fed to reactor 104 is consumed in reactor 104. Accordingly, an additional supply of olefin feedstock is introduced from line 102 through line 118 into line 106 for feed to reactor 120.

A portion of the effluent in line 106 is withdrawn via line 108 and is fed to lights distillation column 110. The overhead from column 110, which is primarily benzene, passes via line 112 through condenser 114 to line 104 were it is admixed with the olefin feed and a portion of the overhead of benzene column 130. Column 110 is a flash column and no reflux is used. A bottoms stream is withdrawn via line 124 from column 110. A portion of the bottoms stream is passed via line 126 through heat exchanger 128 and back to the lower portion of column 110.

Returning to the second alkylation reactor 120, effluent is withdrawn from the reactor via line 122 and passed to benzene column 130. The bottoms stream from column 110 is passed via line 124 to line 122 and is also sent to column 130. A benzene overhead is withdrawn from column 130 via line 132 and condensed in condenser 134. A portion of the overhead is sent back to the top of column 130 and the remaining portion is passed via line 136 to line 102. A bottoms stream is withdrawn from column 130 via line 138. A portion of this bottoms stream is passed via line 140 through heat exchanger 142 and returned to column 130 to supply heat for the distillation.

Figure 2:
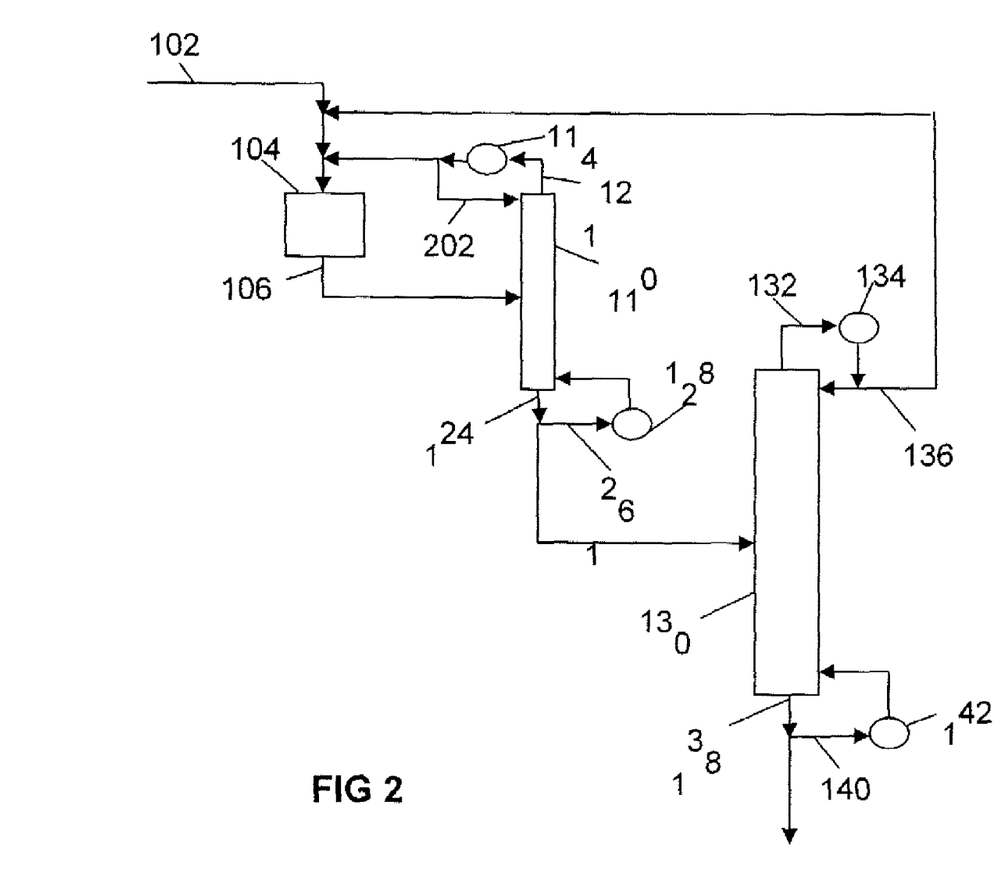
FIG. 2 is a schematic representation of an apparatus adapted to practice a process in accordance with this invention having a single alkylation reactor.

In FIG. 2, the same numerical indicators indicate the same components as are identified for FIG. 1. The apparatus depicted in FIG. 2 differs from that in FIG. 1 in that no second alkylation reactor 120 is used and the bottoms stream from column 110 is passed via line 124 to benzene distillation column 130. Thus, the entire effluent from alkylation reactor 104 is passed via line 106 to lights distillation column 110. Also, a portion of the condensed liquid in line 112 is returned via line 202 to the top of column 110 as reflux. Column 110 contains structured packing.

Figure 3:
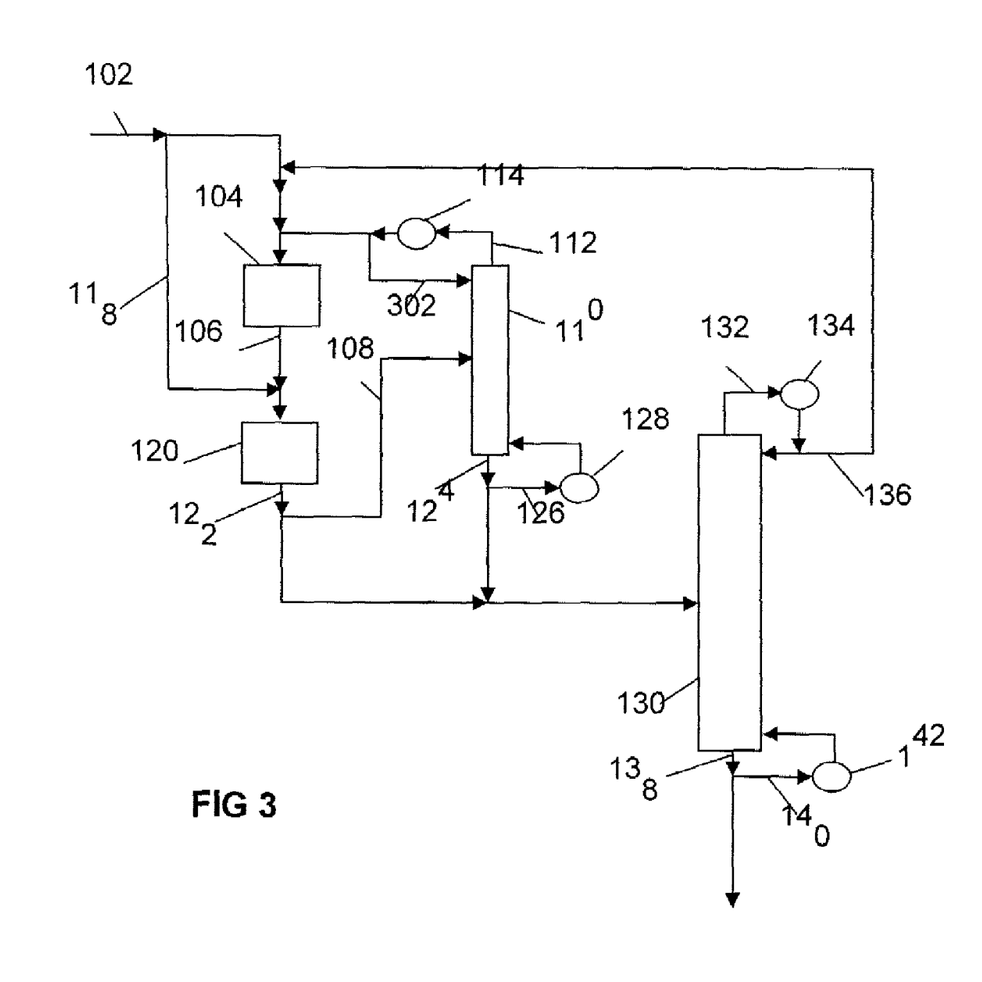
FIG. 3 is a schematic representation of another apparatus adapted to practice a process in accordance with this invention in which two alkylation reactors are provided and the feed for the lights distillation is obtained from the effluent from the second reactor and the overhead from the lights distillation is recycled to the first reactor.

In FIG. 3, the same numerical indicators indicate the same components as are identified for FIGS. 1 and 2. The apparatus depicted in FIG. 3 differs from that in FIG. 1 in that line 108 withdraws a portion of the reaction effluent not from reactor 104 but from reactor 120. A portion of the overhead from lights distillation column 110 is recycled to alkylation reactor 104. Also, a portion of the condensed liquid in line 112 is returned via line 202 to the top of column 110 as reflux. Column 110 contains packing.

Figure 4:
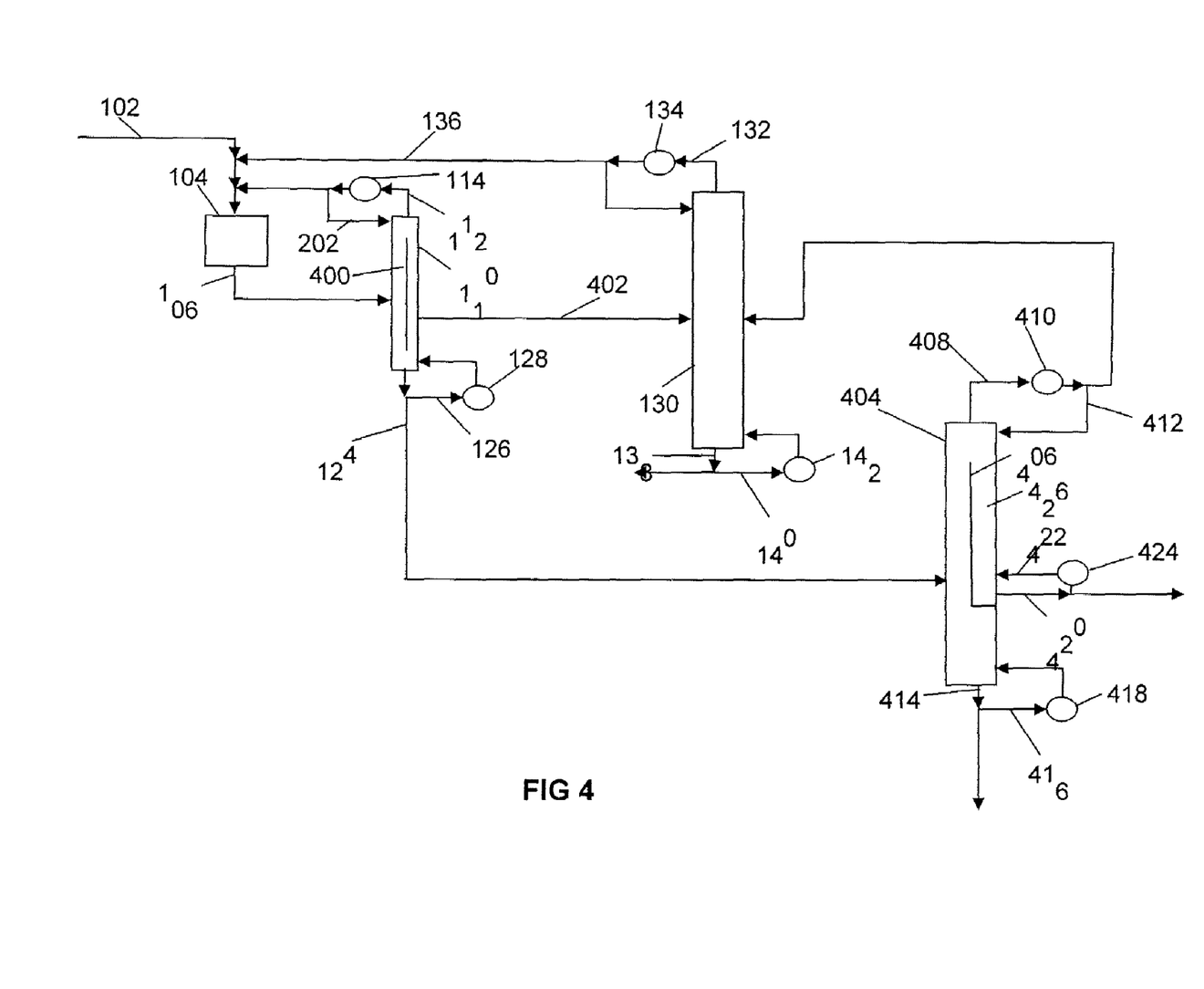
FIG. 4 is a schematic representation of still another apparatus adapted to practice a process in accordance with this invention in which a side stream cut is taken form the lights distillation. This representation illustrates further distillations to provide a purified arylalkane product.

In FIG. 4, the same numerical indicators indicate the same components as are identified for FIG. 2. The apparatus depicted in FIG. 4 differs from that in FIG. 2 in that column 110 is a trayed, dividing wall column having partition 400. On the opposite side of column 110 from the point of introduction of the alkylation reactor effluent, a midcut is removed via line 402. This midcut contains benzene and paraffin and is passed to benzene column 130. The bottoms stream from column 130 will contain little alkylbenzene and will be rich in paraffin. Thus a portion of the bottoms stream in line 138 can be returned to a paraffin dehydrogenation unit.

The bottoms stream from lights distillation column 110 is passed via line 124 to heavies column 404. Heavies column 404 provides an overhead containing benzene and paraffin which is withdrawn via line 408, condensed in condenser 410 and a portion is returned via line 412 to column 404 as reflux and the remaining portion is passed via line 408 to benzene column 130. The bottoms stream from column 404 contains heavies such as dialkyl benzene and is withdrawn via line 414. A portion of the bottoms stream is passed via line 416, heated in heat exchanger 418, and returned to the bottom portion of column 404. Column 404 is also provided with partition 406, which defines a zone 426. Zone 426 can perform as a column within column 404. An alkylbenzene stream is withdrawn via line 420 from the bottom of zone 426. A portion of this alkylbenzene stream in line 420 is returned to the lower portion of the partitioned zone 426 via line 422 having heat exchanger 424. The remaining portion of the stream in line 420 is product.

The invention claimed is:

1. An apparatus for the alkylation of an aromatic compound with an olefin-containing aliphatic compound comprising:
   a. an alkylation reactor having an alkylation reactor inlet portion in fluid communication with a supply of olefin-containing aliphatic compound and an alkylation reactor outlet portion, said alkylation reactor having a chamber, said chamber being such that fluid passing between said alkylation inlet portion and said alkylation reactor outlet portion passes through said chamber, said chamber being adequate to contain solid alkylation catalyst;
   b. a first distillation column having a first inlet in fluid communication with said alkylation reactor outlet portion, a first overhead outlet, comprising the aromatic compound in an amount between 20 and 98%, in fluid communication with said alkylation reactor inlet portion, and a first bottoms stream outlet, said first distillation column having less than 5 theoretical distillation plates; and
   c. a second distillation column having a second inlet in fluid communication with the first bottoms stream outlet, a second overhead outlet in fluid communication with said alkylation reactor inlet portion, and a second bottoms stream outlet, said second distillation column having greater than 5 theoretical distillation plates;
   wherein said alkylation reactor comprises a preceding reactor and at least one subsequent reactor in series, said preceding reactor having a preceding reactor inlet portion and a preceding reactor outlet portion, said at least one subsequent reactor having a subsequent reactor inlet portion and a subsequent reactor outlet portion, wherein said subsequent reactor inlet portion is in fluid communication with said preceding reactor outlet portion, said preceding reactor outlet portion is in fluid communication with said first distillation column, and said first overhead outlet is in fluid communication with said preceding reactor inlet portion.

2. The apparatus of claim 1 in which said first distillation column is a flash distillation column.

3. An apparatus for the alkylation of an aromatic compound with an olefin-containing aliphatic compound comprising:

a. an alkylation reactor having an alkylation reactor inlet portion in fluid communication with a supply of olefin-containing aliphatic compound and an alkylation reactor outlet portion, said alkylation reactor having a chamber, said chamber being such that fluid passing between said alkylation inlet portion and said alkylation reactor outlet portion passes through said chamber, said chamber being adequate to contain solid alkylation catalyst;

b. a first distillation column having a first inlet in fluid communication with said alkylation reactor outlet portion, a first overhead outlet, comprising the aromatic compound in an amount between 20 and 98%, in fluid communication with said alkylation reactor inlet portion, and a first bottoms stream outlet, said first distillation column having less than 5 theoretical distillation plates; and c. a second distillation column having a second inlet in fluid communication with the first bottoms stream outlet, a second overhead outlet in fluid communication with said alkylation reactor inlet portion, and a second bottoms stream outlet, said second distillation column having greater than 5 theoretical distillation plates;

wherein said alkylation reactor comprises a preceding reactor and at least one subsequent reactor in series, said preceding reactor having a preceding reactor inlet portion and a preceding reactor outlet portion, said at least one subsequent reactor having a subsequent reactor inlet portion and a subsequent reactor outlet portion, wherein said subsequent reactor inlet portion is in fluid communication with said preceding reactor outlet portion, said subsequent reactor outlet portion is in fluid communication with said first distillation column, and said first overhead outlet is in fluid communication with said preceding reactor inlet portion.

4. The apparatus of claim 3 wherein said subsequent reactor inlet portion is in fluid communication with a supply of olefin-containing aliphatic compound.

5. The apparatus of claim 3 in which said first distillation column is a flash distillation column.

* * * * *